(12) United States Patent
Bernstein et al.

(10) Patent No.: US 9,289,286 B1
(45) Date of Patent: Mar. 22, 2016

(54) HAIR TRANSPLANT PROCEDURE WITH A TIME DELAY BETWEEN IMPLANT SITE PREPARATION AND GRAFT IMPLANTATION

(76) Inventors: Robert Michael Bernstein, New York, NY (US); William R. Rassman, Studio City, CA (US)

(*) Notice: Subject to any disclaimer, the term of this patent is extended or adjusted under 35 U.S.C. 154(b) by 939 days.

(21) Appl. No.: 13/453,977

(22) Filed: Apr. 23, 2012

Related U.S. Application Data

(60) Provisional application No. 61/478,052, filed on Apr. 21, 2011.

(51) Int. Cl.
*A61F 2/10* (2006.01)
*A61B 17/34* (2006.01)
*A61B 17/00* (2006.01)

(52) U.S. Cl.
CPC .............. *A61F 2/10* (2013.01); *A61B 17/3468* (2013.01); *A61B 2017/00752* (2013.01)

(58) Field of Classification Search
CPC .............. A61B 17/0057; A61B 2017/00752; A61B 2017/00969; A61B 2018/00476; A61F 2/10; A61K 35/36; A61Q 7/00; A61N 5/0617
See application file for complete search history.

(56) References Cited

U.S. PATENT DOCUMENTS

| | | | |
|---|---|---|---|
| 4,160,453 A | 7/1979 | Miller | |
| 4,346,713 A | 8/1982 | Malmin | |
| 5,137,533 A * | 8/1992 | Giampapa | 623/15.11 |
| 5,545,224 A * | 8/1996 | Israelsen | 128/898 |
| 5,562,613 A | 10/1996 | Kaldany | |
| 5,868,758 A * | 2/1999 | Markman | 606/133 |
| 6,059,807 A | 5/2000 | Boudjema | |
| 6,461,369 B1 | 10/2002 | Kim | |
| 7,144,406 B2 | 12/2006 | Pak | |
| 2004/0193203 A1 | 9/2004 | Pak | |
| 2006/0293703 A1 | 12/2006 | Pak | |
| 2007/0243153 A1* | 10/2007 | Ustuner | 424/70.1 |
| 2008/0051816 A1 | 2/2008 | Pak | |
| 2009/0220579 A1* | 9/2009 | Hassingboe et al. | 424/445 |
| 2011/0130711 A1* | 6/2011 | Lederman et al. | 604/22 |

OTHER PUBLICATIONS

Dow B. Stough M.D., Hair Replacement Surgical and Medical, 1996, pp. 147-149, Mosby-Year Book Inc, USA.
Robert M. Bernstein M.D., Integrating Robotic FUE into a Hair Transplant Practice, Hair Transplant Forum International, 2012, 228-229, 22(6).
Robert M. Bernstein M.D., Pre-Making Recipient Sites to Increase Graft Survival in Manual and Robotic FUE Procedures. Hair Transplant Forum International, 2012, 128-130, 22(4).

* cited by examiner

*Primary Examiner* — Alexander Orkin
(74) *Attorney, Agent, or Firm* — Lawrence S. Cohen

(57) ABSTRACT

The method of implanting hair grafts in which implant wounds are made at sites for implanting the hair grafts and the implantation is delayed while the implant wounds are allowed a period to heal. The period for healing may be at least 18 hours after the wounds are made.

13 Claims, 2 Drawing Sheets

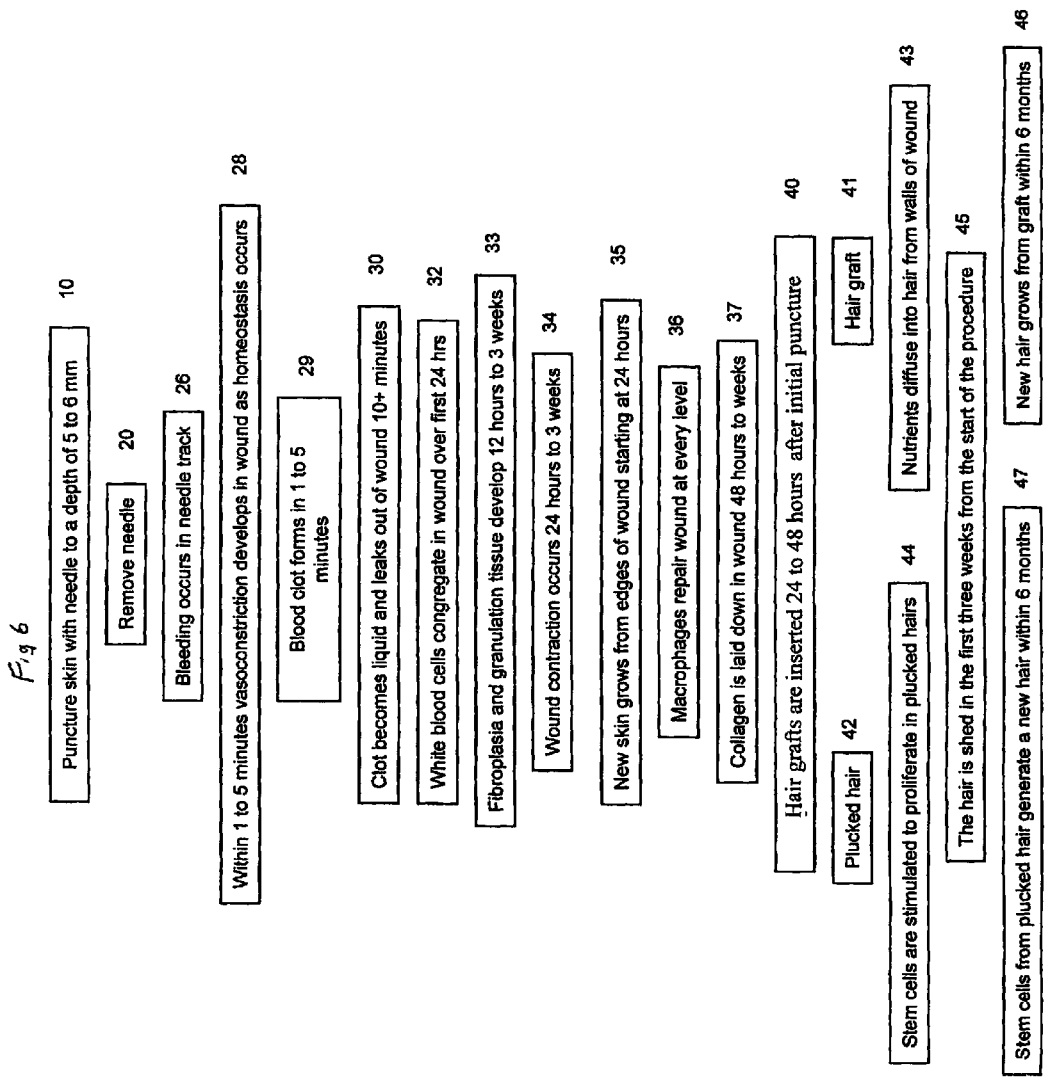

HAIR TRANSPLANT PROCEDURE WITH A TIME DELAY BETWEEN IMPLANT SITE PREPARATION AND GRAFT IMPLANTATION

RELATED APPLICATIONS

This application is related to Provisional Application Ser. No. 61/478,052 filed on Apr. 21, 2011 from which priority is claimed.

FIELD OF THE INVENTION

This invention relates to procedures for harvesting and transplanting human hair.

BACKGROUND OF THE INVENTION

The current method for hair transplantation is a four-part process completed in a single, 1-day session. These four overlapping steps include: (1) hair follicle grafts or follicular unit grafts (naturally occurring groups of 1-4 hairs) are harvested from the permanent donor area, either in a long-thin strip that is subsequently dissected into follicular units (follicular unit transplantation via strip method) or removed directly from the scalp one at a time (follicular unit extraction), (2) grafts are held in a chilled, physiologic solution, (3) needle-size wounds are made in a recipient area, and (4) follicular unit grafts are placed into the recipient sites.

In 1994, Dr. Richard Shiell proposed the concept of an X Factor, some unknown factor (or factors) which can lead to sub-optimal growth following a hair transplant. Over the years, as these "unknown" factors have been identified and addressed, graft survival has improved. Some of these factors that have been responsible for the improvements in growth have included: (a) minimizing surgical transection of the follicles at the time of harvesting, (b) preventing graft desiccation and warming, (c) reducing the time grafts are in the oxygen and nutrient poor environment outside the body, and (d) decreasing crush injury during placing.

In 1997, Dr. Bobby Limmer underscored the time concern by reporting decreased survival when grafts spend prolonged periods of time outside the body. Following that work, there has been a significant effort to streamline the surgical process so that grafts could be planted as quickly as possible—a particular concern in large surgical sessions. Graft survival has been enhanced by cooling the graft holding solution to temperatures ranging from 40 to 60° F. There have also been advances in the way grafts are stored, using special solutions that nourish the grafts, so that they are in a more physiologic environment while awaiting placement into the recipient sites.

SUMMARY

One of the first responses to the creation of a recipient wound, like any wound to the body, is the formation of a clot, an event that begins well before oxygen and nutrients diffuse into the wound. This has great adaptive value for an organism, where the immediate containment of blood loss takes precedent over the healing process, but presents a problem for newly transplanted grafts that have been sitting in a holding solution deprived of oxygen.

Modern hair transplant procedures use a "snug fit" between a freshly placed graft and the recipient wound into which it is placed. This increases contact between the surface of the graft and the walls of the recipient site, minimizing dead space and reducing clot formation around the graft. This promotes diffusion of oxygen and nutrients into the newly transplanted tissue which, in turn, will facilitate optimal graft survival. However, the presence of any coagulum may still interfere with the survival of the delicate follicular unit graft.

It has been assumed that once follicular unit grafts are transferred from the cold, hypoxic environment of a holding solution, into the warm milieu of the human scalp, its metabolic needs would immediately be fulfilled by the diffusion of oxygen and nutrients from the walls of the wounds. However, although vasodilation occurs with ten minutes of wounding, the reabsorption of the clot, the mobilization of an inflammatory infiltrate, the formation of granulation tissue and angiogenesis takes hours to days to develop.

Another aspect of the hair transplant procedure that can adversely affect the survival of grafts is crush injury during placement. When grafts are placed in newly made recipient sites they tend to pop up, or completely out, due to the active blood flow and the slippery nature of the wound edges. This necessitates re-insertion, subjecting the grafts to additional injury. In addition, the popped grafts sitting above the skin surface (awaiting replacement) are more subject to desiccation and hypoxic injury compared to grafts still in their chilled, holding solution.

Over time, the bleeding subsides and the wound edges become more "sticky" due to activation of the coagulation cascade. This enables grafts to be placed more easily, so that the later part of the placement process proceeds with greater ease than the initial phases. To take advantage of this natural phenomena, graft placement performed the day following recipient site creation facilitates the procedure, as there is minimal to no bleeding or popping of inserted grafts.

This invention overcomes the limitations of the current hair transplant procedure with respect to the normal biologic progression of healing wounds, by introducing a time-delay between recipient site creation and graft insertion in order to facilitate graft placement and enhance graft survival.

In current hair transplant procedures, a relatively short period of time passes between the actual harvesting and implantation of hair grafts into the recipient wounds. Additional time passes before the transplanted grafts are oxygenated by the body. It is presently believed that the quicker the process from graft harvesting to graft placement, the higher the level of successful growth of the transplanted grafts.

In accordance with this invention; 1) the time from graft harvesting to graft placement is decreased, 2) graft placement is facilitated so that it can occur with less injury to grafts, and 3) the recipient sites are prepared sufficiently in advance of placement, so that the relatively hypoxic clot formation phase of wound healing and the other early phases of wound healing are timed to occur before the movement of the transplanted hair graft into the recipient sites.

To accomplish this, needle-size wounds are made in a plurality of positions in the recipient area, to a depth in the scalp common for accepting follicular unit grafts, an exemplary period of approximately 24 hours (typically one day) prior to graft harvesting. This allows the extracted or dissected strip-harvested grafts to be immediately placed into the recipient wounds and for these wounds to be at a point in the healing process which is already well underway.

BRIEF DESCRIPTION OF THE DRAWINGS

FIG. 6 is a flow diagram of the method according to this invention.

DEFINITIONS

Figure 1:
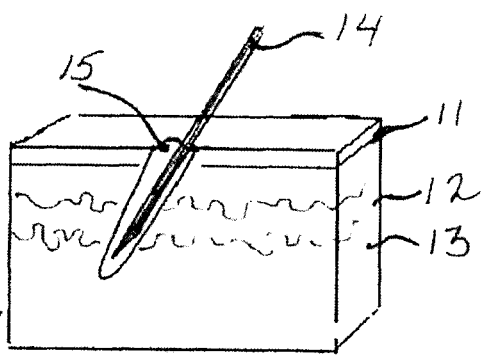
FIGS. 1-5 are schematic representations of the status of a representative implant sight during the method in accordance with the principles of this invention.
Figure 2:
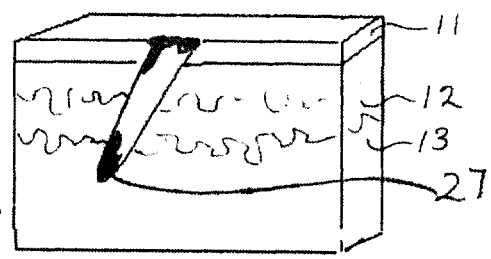
Figure 3:
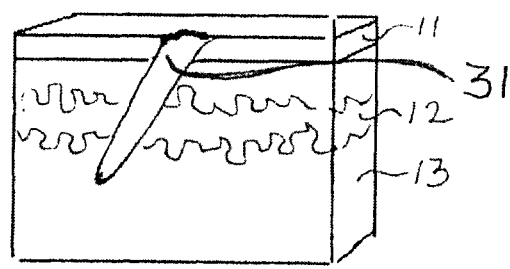
Figure 4:
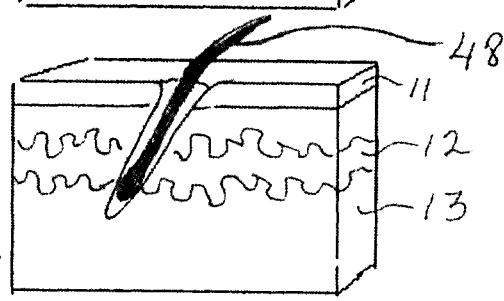

Extracellular matrix (ECM): The Extracellular Matrix is the extracellular part of animal tissue that usually provides structural support to the animal cells in addition to performing various other important functions. The extracellular matrix is the defining feature of connective tissue in animals and includes the interstitial matrix and the basement membrane of the tissue. Interstitial matrix is present between various animal cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest.

Hair Graft: This reflect part or all of the anatomical structures of individual hairs, singly or in groups of more than one hair follicle, (i.e. a follicular unit).

Neovascularization: Neovascularization is the formation of functional microvascular networks in living tissues amongst groups of cells with red blood cell perfusion.

Mesenchymal Cells: Mesenchymal Cells are multipotent stem cells that can differentiate into a variety of cell types.

Hypoxic: Reflects a lack of oxygen in some living cells or tissues.

DETAILED DESCRIPTION OF THE INVENTION

It is well known that when a hair is plucked from the body, the plucked area re-grows a new hair. That happens because the important anatomical structures necessary for growth remain in the plucked area. If the actual plucked hair could generate a fully grown hair, that would mean that a person who had one hair plucked from its donor site would develop two hairs (one from the plucked hair area which would re-grow the original hair and one from elements of the plucked hair which could be stimulated to grow a second hair). In other words, from one hair, two hairs would be derived.

Plucked hair has recently been shown to re-grow a new hair in a new location provided that it is stimulated to grow. If a hair is plucked, one can observe some tissue along the sides of the actual plucked hair shaft. This is believed to reflect stem "type" cells that come out when the hair is plucked. One researcher reported that the stimulus for this growth can be induced by an extra-cellular matrix (ECM) derived from porcine urinary bladder. ECM has been successfully used to stimulate rapid tissue remodeling by promoting neovascularization and by recruiting host-derived mesenchymal cells and a variety of growth factors to the site of the man-made wound. The use of a commercially available Extra-cellular Matrix material may facilitate the healing of wounds and it has been used in wounds made in various body parts in association with surgical procedures (FDA approved for this purpose).

This application teaches that needle wounds made in advance of a hair transplantation process that allow for the commencement of wound healing, would also facilitate this regenerative process. When used in the recipient area approximately 24 hours (or more) in advance of placing plucked hairs, these wounds would create the most fertile bed for hair multiplication and hair regeneration derived from stem cell debris material found on a plucked or transplanted hair grafts thus, making recipient sites in advance of graft harvesting in a traditional follicular unit hair transplant procedure would enhance graft survival for the reasons just described.

The method of this invention is designed to capitalize upon the fact that a significant amount of metabolic and cellular activity takes place during the first 24 hours following the creation of any wound. The use of extracellular matrix (ECM) can enhance the process of mesenchymal activation and the activation of stem cell formation.

This process increases the permeability of blood vessels allowing fluid, nutrients and growth factors to flow into the wound. The clots that formed at the time of the wounding are reorganized over time and the diffusion of oxygen into the wound follows increased vascular permeability that brings in a host of factors that can potentially facilitate the growth of a transplanted graft or fragment of a graft such as found in a plucked hair.

FIGS. 1 through 5 are schematic representations depicting the status of an illustrative hair graft implant position during an implant procedure in accordance with the principles of this invention. The method and wound status are represented in the flow diagram of FIG. 6.

Specifically, the procedure commences with the puncturing of the scalp in each of a plurality of positions in the selected area of the scalp. This step is represented in FIG. 6 by block 10. The needle in each position is inserted to a depth of about 6 mm through the epidermis 11, the reticular dermis 12, into the fatty dermis 13 as shown in FIG. 1. The needle in FIG. 1 is designated 14 and the resulting skin wound is designated 15. The needle 14 is removed as indicated by block 20 in FIG. 6. Bleeding occurs in each wound as indicated by block 21 in FIG. 6 and at 27 in FIG. 2.

Within 1 to 5 minutes after the needle is withdrawn vasoconstriction develops as homeostasis occurs. This is represented by block 28 in FIG. 6. A blood clot forms in from 1 to 5 minutes as indicated by block 29 in FIG. 6. The clot becomes liquid and leaks out of the wound in ten or more minutes as indicated by block 30 of FIG. 6 and by the "clear" wound 31 depicted in FIG. 3. White blood cells congregate in the wound over the first 24 hours as indicated by block 32 in FIG. 6.

The neutral repair of a wound is set forth with reference to blocks 33 through 37 in FIG. 6. Specifically, fibroplasia and granulation tissue develop in from 12 hours to 3 weeks as indicated by block 33. Wound contraction occurs in from about 24 hours to 3 weeks as indicated by block 34 and new skin grows from the edges of each wound starting in about 24 hours as indicated by block 35. Macrophages repair each wound at every level starting at about 24 hours as indicated by block 36. Collagen is laid down in each wound in from 48 hours to weeks as indicated by block 37.

The preferred window for graft implantation in a wound opens at about 24 hours after the wound is made—at a time corresponding to block 35 and remains open for another 24 hours to a few days. The graft insertion period is indicated by block 40 in FIG. 6.

Figure 5:
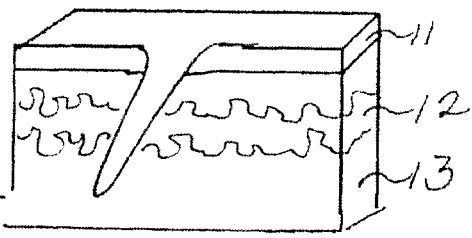

The hair graft for implantation may be harvested by a familiar coring needle or, preferably, by the plucking of individual hairs or follicular units. This is indicated by blocks 41 and 42 in FIG. 6. For cored out grafts, nutrients diffuse into the grafts from the walls of the wound as indicated by block 43. For plucked hairs, stem cells are stimulated to proliferate as indicated by block 44. In either case, the implanted hair, or follicular unit, is shed from a wound in the first 3 weeks as indicated by block 45. The wound is then free of the implanted hair as represented in FIG. 5.

New hair grows from the graft within 6 months as indicated by block 46 in FIG. 6 and stem cells from plucked hairs or follicular units generate new hair also within 6 months as indicated by block 47.

According to the principles of the present invention a method is described for transplanting hair grafts or plucked hair from a donor region of a patient's scalp to a recipient region of the patient's scalp. The system of the present invention differs from traditional hair transplantation as the wounds with this invention are made in advance of the placement of the donor hair by a time-frame ideally in excess of 24 hours. FIG. 6 describes what the human body does in reaction a wound in the scalp.

In summary, considerable changes occur over time in the wound as a result of a healing process that commences at the time the wound is made. Within the first 5 to 10 minutes after the formation of the wound, considerable amounts of the blood clot becomes liquid and leaks out of the wound. White blood cells congregate in the wound to create a defensive barrier to prevent infection. Cells related to the white blood cells (macrophages) immediately congregate into the wound to begin cleaning up the wound of any debris that may be present. The process of fibroplasia begins and the deposition of specialized granulation tissue gets put down in the walls of the wound within the first 24 hours and this process and it continues over the ensuing weeks. New blood vessels begin to develop (neovascularization) to bring oxygen to feed the body as to repair the tissues.

In the early phases of this process, approximately 24-48 hours, the hair graft or plucked hair is placed into the wound (the time interval between FIG. 3 and FIG. 4) as the repair process has commenced. The delivery of nutrients and needed oxygen increase with time as more blood flow develops into the vicinity of the wound within the first 24-48 hours. At this time (24-48 hours after the needle wound is made) the graft or plucked hair is placed into the wound. The repair of the wound incorporates the graft or plucked hair almost immediately after placement. The graft or plucked hair becomes secure in the hole within 24 hours after it is placed and remains there as the wound healing continues. The actual graft or plucked hair will usually be expelled from the hole between 3-6 weeks after placement. Stem cells from the graft or plucked hair will stimulate the growth of a new hair at the point where it was placed. For each hair within a graft or each plucked hair, a new hair (one for one) will begin to grow from the recipient area in 3-6 months.

Experimentation has indicated that transplantation in accordance with the principles of this invention are successful virtually 100 percent of the time (as compared to approximately 80 percent with present state of the art procedures) when grafts and/or plucked hairs or follicular units are harvested and quickly implanted in partially healed wounds in the times indicated in block 40. It is to be understood that in each instance, a wound is made and a relatively lengthy minimum time period elapses before hair is harvested for quick implantation into the wound.

The process of wound healing proceeds through a number of stages as indicated in connection with FIG. 6. But the timing at which each stage in the process commences does vary.

The preferred window for implantation occurs between 24 and 48 hours after the wounds are made at a time when the wounds are clearly well into the process of healing. It is to be understood that the initiation of the implant procedure could be started prior to the 24 hour period still in accordance with the principles of this invention. But the risk of implant failure increases in proportion to the initiation of the implantation procedure prior to the 24 hour window by the period 15 hours after the wounds are made. The rate of successful implants appears to be no better than the success rate of prior art procedures. It appears that a beneficial improvement in successful implants over prior art success rates is still obtained at least 18 hours after the wounds are made.

The foregoing Detailed Description is presented for purposes of illustration and disclosure in accordance with the requirements of the law. It is not intended to be exhaustive nor to limit the invention to the precise form(s) described, but only to enable others skilled in the art to understand how the invention may be suited for a particular use of implementation. The possibility of modifications and variations will be apparent to practitioners skilled in the art. No limitation is intended by the description of exemplary embodiments which may have included tolerances, feature dimensions, specific operating conditions, engineering specifications or the like and which may vary between implementations or with changes to the state of the art and no limitation should be implied there from. This disclosure has been made with respect to the current state of the art, but also contemplates advancements and that adaptations in the future may take into consideration those advancements, namely in accordance with the then current state of the art. It is intended that the scope of the invention be defined by the claims as written and equivalents as applicable. Reference to a claim element in a singular is not intended to mean "one and only one" unless explicitly so stated. Moreover, no element, component nor method or process step in this disclosure is intended to be dedicated to the public regardless of whether the element, component or step is explicitly recited in the Claims. No claim element herein is to be construed under the provisions of 35 USC Sec. 112, sixth paragraph, unless the element is expressly recited using the phrase "means for . . . . " And no method or process step herein is to be construed under those provisions unless the step, or steps, is expressly recited using the phrase "step(s) for . . . . "

What is claimed is:

1. The method of transplanting hair grafts from harvesting sites to a transplant area comprising:
   a. inserting a needle into each of a plurality of implant sites in a selected transplant area for forming a pattern of needle wounds;
   b. allowing a period for the process of wound healing to occur for the resulting pattern of wounds said period being not sooner than about 24 hours after the pattern of wounds is made;
   c. after said period, when the wounds are in the process of healing initiate commencing the implantation of individual extracted hair grafts.

2. The method of claim 1 wherein the implantation of hair grafts from harvesting sites is initiated within about 24-48 hours after the pattern of wounds is made.

3. The method of claim 1 wherein each wound is made into the subdermal layer of the scalp to a depth about that of the length of a mature hair shaft.

4. The method of claim 3 wherein each wound is made to a depth of about 4-6 mm.

5. The method of claim 1 comprising the step of applying an extra-cellular matrix over the pattern of wounds for promoting wound healing in advance of implantation of hair grafts.

6. The method of claim 5 wherein the extra-cellular matrix comprises porcine urinary bladder.

7. The method of claim 1 wherein the implanting of extracted hair grafts commences no sooner than from about 24 hours to several days after the pattern of wounds is made.

8. The method of claim 1 wherein during the period an extra-cellular matrix is applied over the pattern of wounds for promoting wound healing.

9. The method of claim 8 wherein the extra-cellular matrix comprises porcine urinary bladder.

10. In a method for transplanting human hair grafts from a harvesting area to an implant area, the steps of:
   forming an entire pattern of wounds in the implant area to define the pattern of implant sites; and
   no sooner than about 24 hours after forming the pattern of wounds, implanting hair grafts from the harvesting area when the wounds are in the process of healing.

11. The method of claim 10 wherein the implantation of hair grafts from the harvesting area is made no later than about 48 hours after forming the pattern of wounds.

12. A method of transplanting hair grafts from harvesting sites to an implant area comprising;
   forming a pattern of wounds in the implant area to define a pattern of implant sites;
   harvesting grafts for implantation after formation of the pattern of wounds;
   implanting the harvested grafts in the wounds at a time after forming of the wound patterns not earlier than about 24 hours after forming the pattern of wounds when the wounds are in the process of healing.

13. The method of claim 12 wherein implanting of the harvested grafts in the wounds is done no later than about 48 hours after forming of the wound patterns.

* * * * *